United States Patent [19]

Dornhagen et al.

[11] Patent Number: 4,885,405

[45] Date of Patent: Dec. 5, 1989

[54] PROCESS FOR THE PRODUCTION OF PURE DIMETHYLETHER AND A CATALYST USED IN THE PROCESS

[76] Inventors: Horst Dornhagen; Hartmut Hammer; Bernd Haas; Ewald Meisenburg, all of Union Kraftstoff, Ludwigshafener Strasse, D-5047 Wesseling, Fed. Rep. of Germany

[21] Appl. No.: 131,112

[22] Filed: Dec. 10, 1987

[51] Int. Cl.$^4$ ............................................. C07C 41/09
[52] U.S. Cl. ................................. 568/698; 585/640; 502/263
[58] Field of Search ............... 585/639, 640; 568/698; 518/713; 502/263

[56] References Cited

U.S. PATENT DOCUMENTS

| | | | |
|---|---|---|---|
| 3,894,102 | 7/1975 | Chang et al. | 208/141 |
| 4,177,167 | 12/1979 | Manara et al. | 502/506 |
| 4,207,424 | 6/1980 | Winnick | 585/640 |
| 4,232,179 | 11/1980 | Valladares Barrocas | 585/639 |
| 4,328,129 | 5/1982 | Huang | 502/316 |
| 4,337,366 | 6/1982 | Fattore et al. | 568/698 |
| 4,375,424 | 3/1983 | Slaugh | 502/342 |
| 4,423,155 | 12/1983 | Bell et al. | 502/244 |
| 4,590,176 | 5/1986 | Hoek et al. | 502/307 |
| 4,598,785 | 6/1986 | Brake | 568/698 |
| 4,602,119 | 7/1986 | Drake | 585/640 |
| 4,605,788 | 8/1986 | Brake | 568/698 |
| 4,684,757 | 8/1987 | Avidan et al. | 585/640 |
| 4,746,761 | 5/1988 | Avidan et al. | 585/640 |

*Primary Examiner*—Anthony McFarlane
*Attorney, Agent, or Firm*—Connolly and Hutz

[57] ABSTRACT

This invention relates to a process for the production of pure dimethylether by catalytic dehydration of methanol in the presence of a $\gamma$-Al$_2$O$_3$-catalyst which contains a small quantity of SiO$_2$.

7 Claims, No Drawings

PROCESS FOR THE PRODUCTION OF PURE DIMETHYLETHER AND A CATALYST USED IN THE PROCESS

BACKGROUND OF THE INVENTION

Up to the development of low pressure methanol synthesis processes dimethylether has been obtained in a quantity of 2-5 weight-% as a side-product in high-pressure methanol production units and has been isolated by destillation from mixtures, which contained additional low boiling side-products.

After introduction of low pressure methanol processes, which yield only negligible quantities of dimethylether, special synthetic processes have been developed, based on the catalytic dehydration of methanol. Numerous processes have been disclosed in the patent literature. For example, according to DE-PS 680 328, aliphatic ethers are obtained by heating alcohols in the presence of zinc chloride.

Other suitable catalysts for the production of ethers from alcohols are according to GB-PS No. 332 756, GB-PS No. 350 010, GB-PS No. 403 402, U.S. Pat. No. 1,873,537 and FR-PS No. 701 335, ferrous and ferric chloride, copper sulfate, stannic and stannous chloride, manganese chloride, aluminum chloride and -sulfate, chromic sulfate, alum, thorium compounds, aluminum oxide, titanium oxide, barium oxide, silica or aluminum phospate.

In "Industrial and Engineering Chemistry", Vol. 41, No. 12, page 2928 (1949) use of bauxite with a $SiO_2$ portion of 4.40 13.99 weight-% is described. In U.S. Pat. No. 3,036,134 an aluminum silicate-catalyst is disclosed for the production of dimethylether from methanol, with a ratio of $Al_2O_3:SiO_2$ of 1 part: 1,35–0,3 parts. The synthesis of dimethylether directly from synthesis gas ($CO+H_2$) has also been described (DE-PS No. 23 62 944, DE-PS No. 27 57 788 and DE-PS No. 32 20 547).

The technically most important catalysts have turned out to be according to DE-PS No. 28 18 831, DE-OS No. 32 01 155, EP-A No. 0 099 676 and EP-A No. 0 124 078 in particular, aluminum oxide and aluminum silicate catalysts with and without doping. In DE-PS No. 28 18 831 a catalyst for the production of dimethylether is disclosed, which can contain any aluminum oxide as a base material, as far as it possesses a sufficiently large surface and additives of 1 to 30 weight-% of rare earthes.

Finally in EP-A No. 0 099 676 a catalyst is disclosed, which contains 1-20 weight-% of $SiO_2$, preferably 1-10 weight-% of $SiO_2$ and more preferably 6 weight-% of $SiO_2$.

Crude dimethylether thus obtained contains reaction water, unreacted methanol as well as small quantities of contaminations, like methyl formate, hydrocarbons, amines and sulfides, carboxylic acids and esters, amides, acetales and others.

In synthesis units of the state of the art, crude dimethylether is worked up in two distillation columns connected in series. In the first column, which operates under pressure, pure dimethylether is obtained. In the second one unreacted methanol is distilled off. Thus in EP-A No. 0 124 078 a process is described, according to which dimethylether is drawn off in a first column, which is operated under pressure as a sidestream, where as in a second column, which is operated under lower pressure, contaminations with boiling points between dimethylether and methanol, are drawn off overhead methanol is obtained in the same column as a sidestream. Catalysts are $Al_2O_3$, $SiO_2$, aluminum silicates and preferably $\gamma$-$Al_2O_3$. The use of $\gamma$-$Al_2O_3$ as a dehydration catalyst is known for many years. (Catalysis, Vol. VII, Ed. P.H. Emmett, Reinhold Publishing Corp., New York (1960), page 140).

Since dimethylether gains increasing importance as a propellant for sprays, very high demands are made with regard to purity. Thus, no irritating substances in dimethylether are permitted in applications like cosmetic, human and household sprays. Furthermore dimethylether has to be free of odour for these applications.

Object of the instant invention therefore was the production of a highly pure dimethylether by and to convert methanol nearly quantitatively into a highly pure product which is suitable for the above named applications.

Applicant has investigated numerous catalysts with regard to their suitability for the production of pure odorless dimethylether, which can be obtained in an economical distillative purification process Applicant has found that most catalysts, including $Al_2O_3$, $\gamma$-$Al_2O_3$, aluminum silicates, silica and others lead to small quantities of strongly smelling substances, which either have to be separated by extensive purification or which can not be separated even by these processes. Although in many cases the constitution of these substances is not known, because they can not be identified by analytical methods, it is known that the starting material, which is refined methanol, contains already numerous contaminations, like dimethylamin, methyl mercaptane, formic acid, formid acid methyl ester, formaldehyde, formaldehyde dimethylacetate, acetic acid and others. These compounds respectively combinations of these compounds may even in traces lead to unpleasant odour in dimethylether.

Applicant has succeeded in solving the problems described above by the instant inventive process. According to the invention highly pure dimethylether is continuously produced by catalytic dehydration of methanol a temperature of 140°–500° C. and a pressure of 1–50 bar in the presence of $\gamma$-$Al_2O_3$-catalyst, which contains a small quantity of $SiO_2$ and distillative workup of the dehydration product.

Applicant has non-obviously found that the inventive catalyst leads to crude dimethylether which can be economically purified by distillation, whereby an odorless dimethylether is obtained in nearly quantitative yield. In the pressure of the inventive catalysts the formation of smelling contaminations is suppressed.

According to the state of the art, the determination of substances with an unpleasant odour is carried out predominantly by empirical methods, in particular by sensory determination by a trained team. Thus, the limit of inconvenience in case of $H_2S$ has for example been identified in the Federal Republic of Germany by 150 persons as 45 $\mu g/m^3$. (Schriftenreihe der Landesanstalt für Immissionsschutz des Landes Nordrhein-Westfalen, Heft 49 (1979), page 77). In those cases, when the limit of perception of odour can be analyzed by instruments, gaschromotography, electric conductivity photometry or fluorescence measurement are applied ("Erdöl und Kohle-Erdgas-Petrochemie, Vol. 32, Nr. 2, Feb. 1975, page 86). The determinations of odour in the instant application are based on sensory methods.

Crude methanol from methanol synthesis units as well as dimethylether produced catalytically from methanol, contain as outlined above, numerous contaminations, with, in some cases, strong odour.

Crude dimethylether which is produced from crude or pure methanol in dimethylether synthesis units, consists of 20 to 80 weight-% of dimethylether and in addition the above named contaminations, reaction water and unconverted methanol. Since the boiling points of the contaminations, for example of dimethyl amine (b.p. 6.9° C.), dimethyl sulfide (b.p. 37.3° C.), methyl mercaptane (b.p. 5.8° C.), formic acid (b.p. 100.75° C.), formic acid methylester (b.p. 31.5° C.), formaldehyde (b.p. −21° C.), formaldehyde dimethyl acetale (b.p. 45.5° C.) or acetic acid methylester (b.p. 56.95° C.), as well as solubilities and vapor pressures are very different and since the intensity of odour of the individual compounds is also very different and in addition numerous azeotropic mixtures are formed, the object of obtaining highly pure dimethylether in high yield by a more economical process compared to the state of the art, is very difficult to achieve.

The investigations of applicant, which have been carried out during several years in numerous test sequences, in laboratory, pilot plant and technical unit, have non-obviously led to the result that highly pure dimethylether can be produced nearly quantitatively by the inventive catalysts.

The inventive catalysts are catalysts of the $\gamma$-$Al_2O_3$-type, which contains in contrast to the catalysts of the state of the art, only very small quantities of $SiO_2$. The inventive catalysts lead to considerably better results than the known catalysts. The catalysts contain 0.0001 to <1 weight-% of $SiO_2$. The preferred $SiO_2$-concentration is 0.001 to 0.5 weight-% and a particularly preferred concentration is 0.001 to 0.2 weight-% $SiO_2$.

Additionally the inventive catalysts may contain other components in small and very small quantities, for example $Na_2O$ or other alkali- and alkaline earth oxides, alkali, alkaline earth- or aluminum sulfate, iron oxide, cobalt oxide, nickel oxide and other compounds.

The reaction in the presence of the inventive catalysts is carried out at a temperature of 140° to 500° C., preferably at 150° to 450° C. and pressure of 1 to 50 bar, preferably of 1 to 25 bar. The reaction may be carried out in the gas or liquid phase, preferably in the gas phase. Preferably the pressure in the synthesis reactor and in the distillation columns where the crude reaction product is worked up are adjusted to each other. Operation is carried out at a liquid hourly space velocity (LHSV) of 0.2–16 1/1 h, preferably of 0.5–13.5 1/1 h.

The inventive process can be operated discontinuously however preferably continues.

Reactors, which can be used for the inventive process may be the known reactors of the state of the art, like fixed bed-, fluid bed- or fluidized bed-reactors, but also modified, new, and improved reactors, which are suited for catalytic reactions.

The reaction in the presence of catalysts, resp. inventive catalysts can be kinetically or thermo-dynamically controlled, dependent on the reaction parameters. As a consequence the corresponding quantities of dimethylether are obtained at the reactor exit besides the respective unconverted quantities of methanol.

EXAMPLES

Work-up of crude synthesis product (3000 kg/h with 65 weight-% of dimethylether) was carried out in examples 1–9 in two succeeding continuously operating distillation columns, the first of which was equipped with 50 valve trays, whereas the second one was a column packed with ceramic Raschig rings. In the first column which was operated at 7 bar, highly pure dimethylether was withdrawn at the 12th tray (from the top of the column) at a reflux ratio of 1:2. Crude product was fed to the column at the 22nd tray. In the second column, unconverted methanol was recovered. The dimethylether synthesis was carried out at 270°–290° C. and a pressure of 10 bar.

In example 1 a $\gamma$-$Al_2O_3$-catalyst was used, which contained 0.018 weight-% of $SiO_2$.

Pure dimethylether was obtained nearly quantitatively, (99.8 weight-% based on methanol converted) which was free of odour.

In example 2 a $\gamma$-$Al_2O_3$-catalyst was used with a $SiO_2$-content of 0.005 weight-%, however a reflux ratio of 1:0.4 was applied and the crude feed to the distillation column contained 80 weight-% of dimethylether.

As in example 1 pure, odourless dimethylether was obtained nearly quantitatively.

In example 3 the synthesis reaction was carried out with a $\gamma$-$Al_2O_3$-catalyst, containing 0.4 weight-% of $SiO_2$.

The same result as in examples 1 and 2 was obtained.

In example 4 the $\gamma$-$Al_2O_3$-catalyst used, contained 0.025 weight-% of $SiO_2$ and 0.02 weight-% of $Fe_2O_3$.

Dimethylether thus obained was free of odour. The yield was nearly quantitative based on methanol converted.

In comparative example 5, example 1 was repeated, however the catalyst contained 6 weight-% of $SiO_2$.

No dimethlether free of odour could be obtained.

In example 6, example 1 was repeated. As a catalyst aluminum silicate was used. No pure, odorless dimethylether could be obtained.

In example 7, example 1 was repeated. As a catalyst a rho-$Al_2O_3$ with 1.4 % of $SiO_2$ was used.

No pure, odorless dimethylether could be obtained.

We claim:

1. Process for the production of dimethylether by catalytic dehydration of methanol at a temperature of 140°–500° C. and a pressure of 0.2 to 50 bar, characterized in that the dehydration is carried out in the presence of a $\gamma$-$Al_2O_3$ catalyst, which contains 0.0001 to less than 1 weight-% of $SiO_2$.

2. Process according to claim 1, characterized in that the catalyst contains 0.001 to 0.5 weight-% of $SiO_2$.

3. Process according to claim 1, characterized in that the catalyst contains 0.001 to 0.2 weight-% of $SiO_2$.

4. Process according to claim 1, characterized in that the dehydration is carried out at a temperature of 140° to 450° C. and a pressure of 1 bar to 25 bar.

5. Process according to claim 1, characterized in that the dehydration is carried out at a liquid hourly space velocity (LHSV) of 0.2–16 1/1 h.

6. Process according to claim 1, characterized in that the dehydration is carried out at a liquid hourly space velocity (LHSV) of 0.5 to 13.5 1/1 h.

7. Process according to claim 1, characterized in that it is carried out continuously.

* * * * *